United States Patent
Kudlaty et al.

(10) Patent No.: US 9,816,854 B2
(45) Date of Patent: Nov. 14, 2017

(54) CAPACITIVE ULTRASONIC TRANSDUCER

(75) Inventors: Katarzyna Kudlaty, Gössendorf (AT); Michael Wiesinger, Graz (AT); Michael Cernusca, Judendorf-Strassengel (AT)

(73) Assignee: AVL List GmbH, Graz (AT)

( * ) Notice: Subject to any disclaimer, the term of this patent is extended or adjusted under 35 U.S.C. 154(b) by 963 days.

(21) Appl. No.: 14/128,951

(22) PCT Filed: Jun. 19, 2012

(86) PCT No.: PCT/EP2012/061702
§ 371 (c)(1),
(2), (4) Date: Mar. 26, 2014

(87) PCT Pub. No.: WO2012/175492
PCT Pub. Date: Dec. 27, 2012

(65) Prior Publication Data
US 2014/0216161 A1    Aug. 7, 2014

(30) Foreign Application Priority Data

Jun. 24, 2011 (AT) .................................. A 929/2011

(51) Int. Cl.
*G01N 29/24*   (2006.01)
*G01H 11/06*   (2006.01)
*B06B 1/02*    (2006.01)

(52) U.S. Cl.
CPC ........... *G01H 11/06* (2013.01); *B06B 1/0292* (2013.01); *G01N 29/2406* (2013.01)

(58) Field of Classification Search
CPC .... G01N 29/2406; G01N 29/24; G01H 11/06; B06B 1/0292; B06B 2201/51; B06B 2201/57

USPC .......................................................... 73/632
See application file for complete search history.

(56) References Cited

U.S. PATENT DOCUMENTS

| 2,868,894 | A | * | 1/1959 | Schultz | H04M 1/03 361/283.4 |
| 3,118,022 | A | * | 1/1964 | Sessler | H01G 7/02 307/400 |
| 3,418,436 | A | * | 12/1968 | Neumann | H04R 1/22 381/174 |
| 4,081,626 | A | | 3/1978 | Muggli et al. | |

(Continued)

FOREIGN PATENT DOCUMENTS

| EP | 2269746 | 1/2011 |
| JP | 201050869 | 3/2010 |

OTHER PUBLICATIONS

English Abstract of JP 201050869.

(Continued)

*Primary Examiner* — Laura Martin
*Assistant Examiner* — Rose M Miller
(74) *Attorney, Agent, or Firm* — Dykema Gossett PLLC

(57) ABSTRACT

A capacitive ultrasonic transducer includes a sensor head having a back plate, the structured front side of which is provided with an insulation layer, and the back side of which is provided with an electrode. In order to achieve an improved construction by means of which increased temperature resistance up to several hundred degrees Celsius can be achieved even in strongly oxidizing and reducing media, the membrane provided as a sound generator is subjected to tensile stress in a planar direction.

15 Claims, 2 Drawing Sheets

(56) References Cited

U.S. PATENT DOCUMENTS

| | | |
|---|---|---|
| 6,026,690 A | 2/2000 | Nakagawa et al. |
| 2007/0180916 A1 | 8/2007 | Tian et al. |
| 2010/0322439 A1 | 12/2010 | Akino |
| 2011/0163630 A1 | 7/2011 | Klootwijk et al. |

OTHER PUBLICATIONS

J.H. Qiu, "Passivity and its breakdown on stainless steels and alloys," Surf. Interface Anal. 2007; 33:830-833.

S.H. Nie et al., "Corrosion of alumina-forming austenitic steel Fe—20Ni—14Cr—3Al—0.6Nb—0.1Ti in supercritical water," Journal Nucl. Mat. 399 (2010) 231-235.

\* cited by examiner

CAPACITIVE ULTRASONIC TRANSDUCER

BACKGROUND OF THE INVENTION

Field of the Invention

The invention relates to a capacitive ultrasonic transducer which includes a sensor head having a back plate, the structured front side of which is provided with an insulating layer and the back side of which is provided with an electrode.

The Prior Art

Today, mainly two types of ultrasonic sensors are used for applications in the air or in gas environments. These are piezo-ceramic and/or capacitive ultrasonic sensors. Apart from the differences in the functional principle and the acoustic characteristic, both types can only be used at moderate temperatures and for non-aggressive media.

There are definitely applications with higher temperatures in which up to now no measurement technology could be used, e.g., in the development of internal combustion engines. Depending on the operating state and the position of the flow sensor in the exhaust gas system, the exhaust gas temperatures in this case can range from −40° C. (e.g., cold start of the engine in the climatic chamber) up to approximately 1000° C. Important is also the fact that the exhaust gas temperature of an internal combustion engine can change rapidly and significantly, e.g., during the load change from engine operation at full load into towing operation. The sensor system used shall be able to withstand this extreme variation in thermal load.

The piezoceramic ultrasonic sensors (latest developments are published, for example, in DE 10040344, DE 4434692, DE 102006026674, DE 102008027970, DE 102009032809 and DE 202004002107) can only be used at temperatures below 350° C. This limitation results from the Curie temperature of the piezo crystals used, which lose their piezoelectric properties after exceeding said temperature. The permanent variations in thermal load can result in material fatigue in these sensors (permanent destruction of the piezo crystals).

Also, conventional capacitive ultrasonic transducers do not have the desired temperature resistance. Their metal-coated membrane stretched over an electrically conductive substrate forms at the same time the insulation layer of an electrical capacitance, wherein the plastic films or membranes from silicon nitride that are usually used as dielectric membrane material cannot meet the temperature requirements, as explained, for example, in D. A. Hutchins, D. W. Schindel, A. G. Bashford, and W. M. D. Wright, "Advances in ultrasonic electrostatic transduction", Elsevier Ultrasonics, Vol. 36, 1998. Also, when using purely metallic membranes, oxidation occurs already at temperatures above 300° C., which, due to the low material thickness of a transducer membrane, results in the rapid destruction of said membrane.

In addition to the thermal resistance of the membrane, the thermal resistances of the usual insulation layers and the electrodes are also not high enough. The high temperature promotes, among other things, electrical disruptive discharges in the insulation layer, which result in permanent destruction of the sensors. The reason for this is the temperature-related restructuring or recrystallization of the insulation layer. In the case of the back electrode, the diffusion of the metal layer into the silicon crystal is accelerated by the high temperature. After a certain time, this results in the complete disappearance of the electrode. Due to the poor adaptation of the thermal expansion coefficient during the varying thermal load, chipping of the insulation layer from the carrier material occurs or the membrane is pulled out of the sensor housing, which means destruction of the sensor.

The object of the invention is an improved construction of an ultrasonic transducer by means of which increased temperature resistance of up to several hundred degrees Celsius can be achieved even in strongly oxidizing and reducing media.

SUMMARY OF THE INVENTION

In order to achieve this object, the transducer is characterized according to the invention in that the membrane is subjected to a tensile stress in the planar direction.

According to a first embodiment, the membrane is pressed in between two rings.

In contrast, an alternative embodiment is characterized in that the membrane is welded to at least one ring.

Advantageously, it is provided that the material of the membrane is selected from the group Ni—Cr alloys, austenitic steels, ferritic steels or "super alloys".

It is in particular of advantage if the membrane consists of a material with a chromium content of at least 16% and an aluminum content of at least 1%.

For achieving the aforementioned object, an embodiment is also suitable in which the insulation layer consists of a material having an amorphous structure.

It is preferably provided here that the insulation layer consists of a plurality of amorphous layers.

The aforementioned object is also achieved by the features according to the invention that the back electrode has a multi-layered structure, wherein at least one layer forms a diffusion barrier to the base material of the back plate, and the surface layer consists of platinum.

Advantageously, it is further provided that the sensor head is designed as an assembly that can be replaced independently of the remaining ultrasonic transducer.

An advantageous embodiment of the ultrasonic transducer according to the invention is characterized in that a heating device for the sound-radiating surface is provided.

A further advantageous embodiment of the ultrasonic transducer is characterized in that the regions above and below the membrane are connected by channels within the transducer.

Here, advantageously, filters are provided in said channels.

A further feature of the invention can be that contacting the back plate of the sensor head is carried out by a spring-loaded pin.

Here, advantageously, a metallic intermediate plate is inserted between the pin and the back plate.

By means of the above features and the specific material selection, a temperature resistance of up to several hundred degrees Celsius can be achieved even in strongly oxidizing and reducing media. In the lower temperature range, the functionality of the transducer is ensured by the use of the transducer heater for avoiding condensate formation. Due to these special properties, the ultrasonic transducer can be used wherever conventional technologies that are available on the market find their limits. An example for this can be ultrasonic flowmeters for process control in the chemical industry or food industry, sensors that are used for precise gas volume measurements off shore and in pipelines, or also in the development of internal combustion engines.

In the following description, the invention is to be explained in more detail by way of example and with reference to the accompanying drawings of preferred exemplary embodiments.

DETAILED DESCRIPTION OF THE DEPICTED EMBODIMENTS

Figure 1:
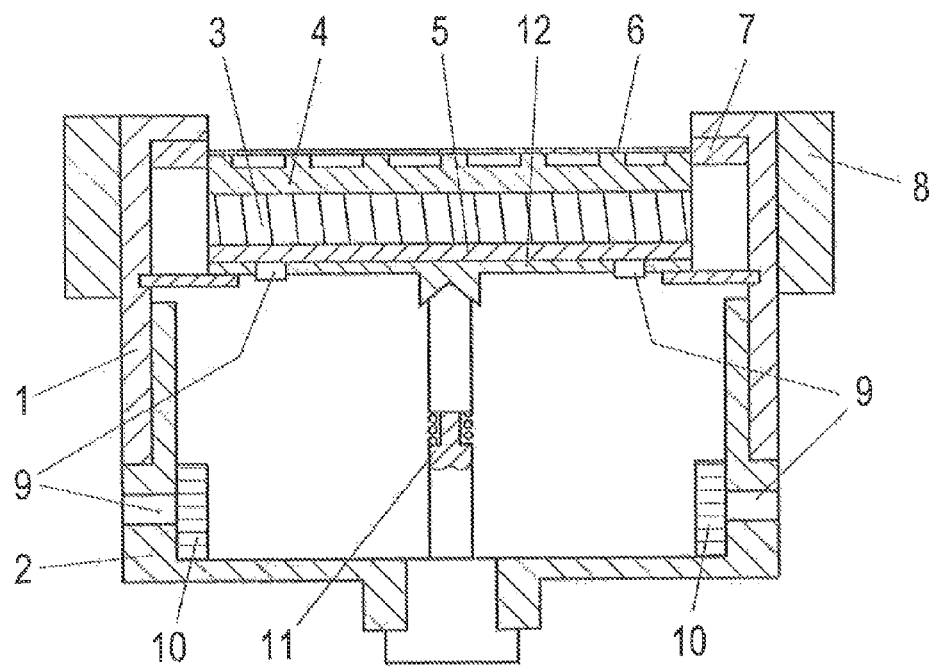
FIG. 1 shows a section through a first embodiment of an ultrasonic transducer according to the invention.
Figure 3:
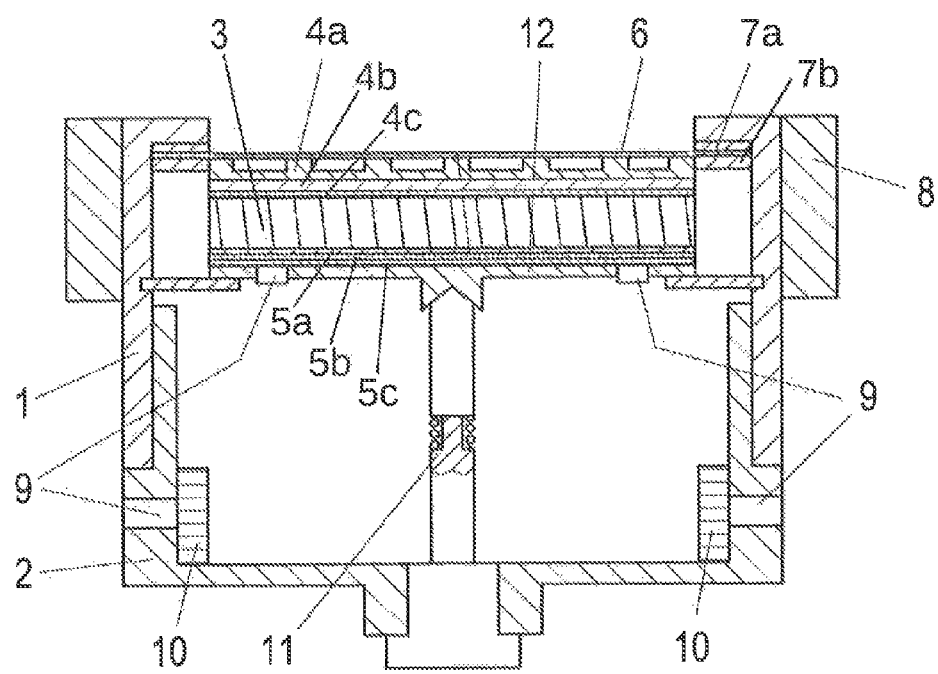
FIG. 3 shows a section through another embodiment of the inventive ultrasonic transducer.

The ultrasonic transducer illustrated below is characterized by its excellent temperature-, oxidation- and corrosion-resistance and has been developed for a wide range of fields of application with high mechanical, thermal and chemical loads. As can be seen in FIG. 1, the sensor head consists of an upper housing part 1 and a lower housing part 2, wherein both parts 1, 2 can be screwed together, or, optionally, can also be connected to one another in a different manner. A back plate 3 has a front side with a structured insulation layer 4, and a back electrode 5 that is applied onto the back side. Here, the insulation layer 4 is made of a material having an amorphous structure, and as seen in the embodiment of FIG. 3, it can include amorphous layers 4a, 4b and 4c. Also as seen in the embodiment of FIG. 3, the back electrode 5 itself can also have a multi-layered structure 5a, 5b and 5c, wherein at least one layer forms a diffusion barrier to the base material of the back plate 3, and a surface layer made of platinum can be provided.

Figure 2:
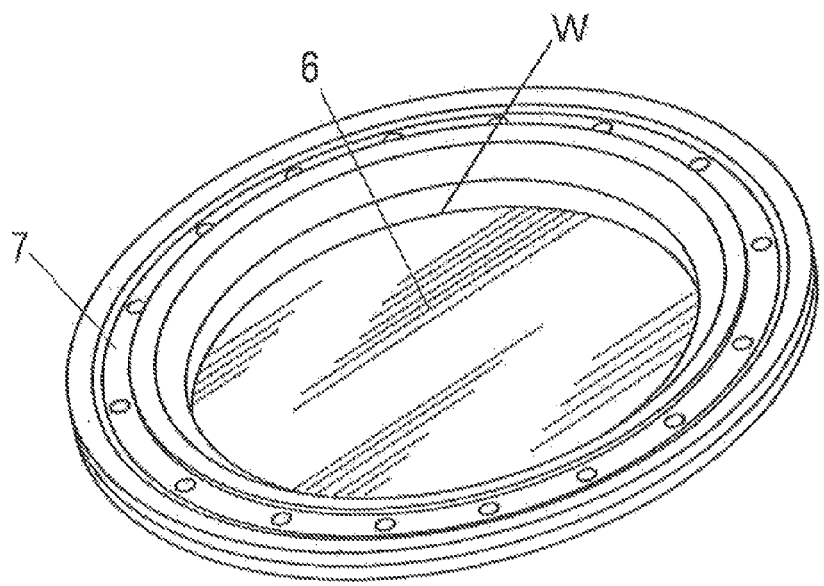
FIG. 2 is a perspective view of an embodiment according to the invention of a pretensioned membrane for such a transducer.

The membrane 6 of the ultrasonic transducer according to the invention is secured in a stretching ring 7, as is also shown in FIG. 2. Through this kind of stretching of the membrane 6, the membrane can be subjected to tensile stress in the planar direction. Specifically, for example, two rings can be provided in-between of which the membrane 6 is pressed (see rings 7a and 7b in FIG. 3), or as shown by weld w in FIG. 2, membrane 6 can be welded to at least one ring 7. The membrane will typically be made of an Ni—Cr alloy, an austenitic steel, a ferritic steel or a "super alloy", wherein advantageously, the chromium content will be at least 16% and the aluminum content will be at least 1%.

In order to avoid condensation during the operation at low temperatures, a heating device 8 is provided that surrounds the upper housing part 1 of the ultrasonic transducer and keeps in particular the sound-radiating surface at the desired temperature.

Channels 9, preferably comprising filters 10, for connecting the regions above and below the membrane 6 are provided both in the housing, in particular in the lower housing part 2, and in rear contacting plate 12 on the back side of the back plate 3 and the back electrode 5. A spring-loaded pin 11 rests against the contacting plate 12 so as to carry out the contacting of the back plate 3 of the sensor head.

Advantageously, the sensor head is designed as an assembly that can be replaced independently of the remaining ultrasonic transducer.

The invention claimed is:

1. A capacitive ultrasonic transducer comprising a sensor including a back plate providing front and back surfaces, a structured insulating layer on said front surface, a membrane forming a sound generator positioned on said structured insulating layer, means for stretching the membrane in a planar direction, and an electrode on said back surface, said electrode including a first layer that forms a diffusion barrier to material of the back plate, and an exposed second layer consisting of platinum.

2. The ultrasonic transducer according to claim 1, wherein the means for stretching the membrane comprises two rings.

3. The ultrasonic transducer according to claim 1, wherein the means for stretching the membrane comprises a ring to which the membrane is welded.

4. The ultrasonic transducer according to claim 1, wherein the membrane consists of a Ni—Cr alloys, austenitic steels, ferritic steels or "super alloys".

5. The ultrasonic transducer according to claim 4, wherein the membrane consists of a material having a chromium content of at least 16% and an aluminum content of at least 1%.

6. The ultrasonic transducer according to claim 1, wherein the insulation layer consists of a material having an amorphous structure.

7. The ultrasonic transducer according to claim 6, wherein the insulation layer consists of a plurality of amorphous layers.

8. The ultrasonic transducer according to claim 1, including a heating device for the membrane.

9. The ultrasonic transducer according to claim 1, including a housing for supporting the sensor head, the housing having channels for providing communication between regions on opposite sides of the membrane.

10. The ultrasonic transducer according to claim 9, including filters for the channels.

11. The ultrasonic transducer according to claim 1, wherein contacting the back plate of the sensor head is carried out via a spring-loaded pin.

12. The ultrasonic transducer according to claim 11, including a metallic intermediate plate between the pin and the back plate.

13. A capacitive ultrasonic transducer comprising a sensor head including a back plate providing front and back surfaces, a structured insulating layer on said front surface, an electrode on said back surface, a membrane forming a sound generator positioned on said structured insulating layer, means for stretching the membrane in a planar direction, and a heating device for heating the membrane.

14. The ultrasonic transducer according to claim 13, wherein the back electrode has a multi-layered structure, wherein at least one layer forms a diffusion barrier to the base material of the back plate, and a surface layer consists of platinum.

15. A capacitive ultrasonic transducer comprising a sensor head including a back plate providing front and back surfaces; a structured insulating layer on said front surface; a membrane forming a sound generator positioned on said structured insulating layer; means for stretching the membrane in a planar direction; an electrode on said back surface; a housing supporting said sensor head; said housing including channels for providing communication between regions on opposite sides of the membrane, and filters for the channels.

* * * * *